(12) United States Patent
Street et al.

(10) Patent No.: US 10,353,083 B2
(45) Date of Patent: Jul. 16, 2019

(54) MONOLITHIC DIGITAL X-RAY DETECTOR STACK WITH ENERGY RESOLUTION

(71) Applicant: Palo Alto Research Center Incorporated, Palo Alto, CA (US)

(72) Inventors: Robert A. Street, Palo Alto, CA (US); Julie A. Bert, Palo Alto, CA (US)

(73) Assignee: PALO ALTO RESEARCH CENTER INCORPORATED, Palo Alto, CA (US)

(*) Notice: Subject to any disclaimer, the term of this patent is extended or adjusted under 35 U.S.C. 154(b) by 0 days.

(21) Appl. No.: 15/702,548

(22) Filed: Sep. 12, 2017

(65) Prior Publication Data

US 2019/0079201 A1    Mar. 14, 2019

(51) Int. Cl.
| | | |
|---|---|---|
| *G01T 1/20* | (2006.01) | |
| *G01T 3/06* | (2006.01) | |
| *H01L 27/146* | (2006.01) | |
| *G01T 1/24* | (2006.01) | |
| *A61B 6/14* | (2006.01) | |

(52) U.S. Cl.
CPC .............. *G01T 1/2018* (2013.01); *G01T 1/24* (2013.01); *G01T 3/06* (2013.01); *H01L 27/1469* (2013.01); *H01L 27/14634* (2013.01); *H01L 27/14663* (2013.01); *H01L 27/14676* (2013.01); *A61B 6/14* (2013.01)

(58) Field of Classification Search
CPC .......... G01T 1/24; G01T 1/2018; G01T 3/06; H01L 27/14634; H01L 27/14663; H01L 27/14676; H01L 27/1469
See application file for complete search history.

(56) References Cited

U.S. PATENT DOCUMENTS

| 5,548,123 | A * | 8/1996 | Perez-Mendez | ...... G01T 1/2018 |
| --- | --- | --- | --- | --- |
| | | | | 250/370.09 |
| 6,380,674 | B1 * | 4/2002 | Aida | ..................... H01J 31/506 |
| | | | | 313/371 |
| 6,392,237 | B1 * | 5/2002 | Agano | ................. G01V 5/0041 |
| | | | | 250/370.11 |
| 7,532,703 | B2 * | 5/2009 | Du | ......................... A61B 6/032 |
| | | | | 378/116 |
| 7,714,287 | B1 * | 5/2010 | James | ................. H01J 37/1472 |
| | | | | 250/306 |
| 8,461,542 | B2 * | 6/2013 | Van Asselt | ............ G01T 1/2928 |
| | | | | 250/370.01 |
| 9,000,382 | B2 * | 4/2015 | Mattson | .................... G01T 1/00 |
| | | | | 250/363.01 |
| 9,649,086 | B2 * | 5/2017 | Tajima | .................... A61B 6/563 |
| 2002/0070365 | A1 * | 6/2002 | Karellas | .................... A61B 6/06 |
| | | | | 250/581 |

(Continued)

*Primary Examiner* — Kiho Kim
(74) *Attorney, Agent, or Firm* — Shun Yao; Park, Vaughan, Fleming & Dowler LLP

(57) ABSTRACT

A monolithic stack of thin x-ray detector layers capable of energy resolution is described. The stack is made of detector layers thinner and closer together than other x-ray detectors, avoiding the need to correct for parallax shifts. Moreover, the system's ability to combine multiple x-ray detector images accurately enables it to resolve x-ray energy information better than existing systems. The system can include a monolithic stack of x-ray detector layers, wherein a respective detector layer contains an x-ray detector and is less than 2 millimeters thick.

17 Claims, 7 Drawing Sheets

(56) References Cited

U.S. PATENT DOCUMENTS

| | | | |
|---|---|---|---|
| 2006/0151708 A1* | 7/2006 | Bani-Hashemi | G01T 1/2008 250/370.11 |
| 2006/0180768 A1* | 8/2006 | Bogdanovich | H01L 27/14676 250/370.09 |
| 2006/0228825 A1* | 10/2006 | Hembree | B23K 20/004 438/51 |
| 2007/0025513 A1* | 2/2007 | Ghelmansarai | A61N 5/1049 378/98.8 |
| 2008/0011960 A1* | 1/2008 | Yorkston | G01T 1/2018 250/370.09 |
| 2009/0054577 A1* | 2/2009 | Uchida | C09D 11/52 524/423 |
| 2010/0193691 A1* | 8/2010 | Ishii | H01L 27/14663 250/366 |
| 2011/0168904 A1* | 7/2011 | Van Asselt | G01T 1/2928 250/370.01 |
| 2011/0215250 A1* | 9/2011 | Ohta | G01T 1/24 250/370.08 |
| 2011/0233415 A1* | 9/2011 | Nakatsugawa | G01T 1/2985 250/370.08 |
| 2011/0309259 A1* | 12/2011 | Kim | G01T 1/24 250/370.09 |
| 2013/0026377 A1* | 1/2013 | Ichimura | G01T 1/202 250/367 |
| 2013/0126743 A1* | 5/2013 | Iwakiri | A61B 6/4216 250/366 |
| 2013/0140464 A1* | 6/2013 | Iwakiri | A61B 6/4283 250/366 |
| 2015/0245807 A1* | 9/2015 | Tajima | A61B 6/563 378/98 |
| 2017/0120077 A1* | 5/2017 | Allinson | A61N 5/1071 |
| 2017/0238887 A1* | 8/2017 | Karim | A61B 6/4241 |
| 2017/0293037 A1* | 10/2017 | Schmidt | G01T 1/2018 |
| 2017/0293039 A1* | 10/2017 | Blenk | G01T 1/244 |
| 2018/0331137 A1* | 11/2018 | Jacob | H01L 27/14603 |
| 2018/0333114 A1* | 11/2018 | Karim | |

\* cited by examiner

MONOLITHIC DIGITAL X-RAY DETECTOR STACK WITH ENERGY RESOLUTION

BACKGROUND

Field

The present disclosure relates to radiation detection. More specifically, this disclosure relates to a monolithic stack of thin x-ray detector layers with improved energy resolution.

Related Art

The dominant technology for medical and other x-ray imaging (such as non-destructive testing) is digital x-ray detection utilizing amorphous Si (a-Si) thin-film transistor (TFT) backplanes. An x-ray generator source typically emits a broad band of x-ray energies, up to a peak energy kVp, which is the accelerating voltage of the generator. The target object absorbs some of the x-ray flux, and the purpose of the detector is to record an image of the transmitted x-ray flux. Typically, a detector has a radiation converter such as a scintillator to convert x-rays to visible light. This light in turn is detected as a pixelated image by a TFT backplane (which typically contains a photodiode and a transistor for each pixel and address lines connecting to the periphery of the backplane). However, such a single-detector system has little capacity for energy resolution. Rather, the single detector responds to the received x-ray energy spectrum according to the scintillator's x-ray absorption.

Energy resolution of x-rays is frequently desirable in order to analyze the nature of target objects being imaged. The energy spectrum of x-ray beams transmitted through a target depends on absorption properties of the materials in the target. Each element has its own specific x-ray absorption spectrum, typically having a peak absorption at some energy (e.g. the element's k-absorption edge) and a decreasing absorption at higher and/or lower energy. Thus, information about the transmitted energy spectrum can assist in identifying constituent materials.

In principle, such energy-resolved information can be obtained by using a stack of multiple detectors. The top detector in the stack (i.e. the detector closest to the x-ray source) is exposed to the full transmitted x-ray spectrum. Yet absorption is typically strongest in the low-energy portion of the spectrum. The next detector therefore is exposed to a different energy spectrum and responds accordingly, producing an x-ray image with a different signal intensity. Energy-resolved information can be obtained by comparing the image signal intensities from the two or more stacked detectors.

However, there are several problems associated with stacking individual detectors for energy resolution. First, the detectors and the associated housings are relatively bulky, so the stacked system may be too bulky for practical usage, especially when more than two detectors are used. Second, each detector is conventionally fabricated on a relatively thick substrate such as glass. Therefore, the stack can contain extra materials that contribute to excess absorption of x-rays, and potentially reduce the overall sensitivity. Finally, the parallax effect can complicate comparison of the images from different detectors in the stack. That is, for detectors separated by a significant spacing, an off-axis x-ray beam transmitted through the target will impinge on different locations in each detector's pixel array. Moreover, the magnitude of this parallax shift depends on the relative positions of the x-ray source and target.

SUMMARY

One embodiment described herein provides a digital detector of ionizing radiation comprising a monolithic stack of multiple adjacent radiation detector layers. A respective detector layer comprises a thin film transistor (TFT) backplane and a radiation converter material. A TFT backplane of a respective detector layer is separated from a converter in an adjacent detector layer by a predetermined minimal distance.

In a variation on this embodiment, respective detectors in two adjacent layers are oriented perpendicularly to facilitate a connection to electronics.

In a variation on this embodiment, a respective layer includes an x-ray energy filter.

In a variation on this embodiment, a respective detector indicates an indirect detector comprising a scintillator and a thin film transistor (TFT) addressable photodiode array.

In a variation on this embodiment, the scintillator comprises gadolinium oxysulphide (GOS) or cesium iodide (CsI), and the TFT addressable photodiode array comprises amorphous silicon (a-Si).

In a variation on this embodiment, a respective detector indicates a direct detector comprising an x-ray photoconductor and a thin film transistor (TFT).

In a variation on this embodiment, the x-ray photoconductor comprises selenium.

In a variation on this embodiment, the stack of x-ray detector layers further indicates a neutron detector.

Another embodiment described herein provides a method for assembling a monolithic stack of x-ray detector layers. The method comprises fabricating a set of thin film transistor (TFT) addressable photodiode or photoconductor backplanes on thin polyimide (PI) layers on a carrier substrate such as glass. The method further comprises attaching a first scintillator in front of the first TFT backplane in the set of TFT backplanes on thin PI layers, wherein the scintillator and first TFT backplane are together less than 2 millimeters thick. The method further comprises attaching a second scintillator to a second TFT backplane in the set of TFT backplanes on thin PI layers. The method further comprises releasing the second TFT backplane from its associated glass substrate, so that the second TFT backplane is supported by the second scintillator. The method further comprises bonding the second TFT backplane on its PI layer in front of the first detector and perpendicularly to the first detector. The method provides a minimal separation between the first and second detector, the separation being the thickness of the PI layer which may be less than 80 micrometers (e.g., as small as 10 micrometers).

In a variation on this embodiment, the method further comprises bonding data connectors and gate drivers to the four sides of the detector stack. For example: the first TFT backplane could be bonded on one side to data connectors and a readout printed circuit board (PCB), using a flex connector or a chip-on-flex (COF) package. Furthermore, the first TFT backplane could be bonded on a second side to a gate driver using a second COF package that does not need immediate attachment to a PCB. Attaching the second TFT backplane comprises bonding data connectors on a third side of the backplane stack to the readout PCB or to a second readout PCB, using a third flex connector or COF package. Attaching the second TFT backplane further comprises bonding a gate driver to the fourth side of the backplane stack using a fourth COF package that does not need immediate attachment to a PCB.

In a variation on this embodiment, the method further comprises releasing the first TFT backplane from its carrier substrate. The method further comprises bonding the first TFT backplane on its PI layer to an alternative substrate.

In a variation on this embodiment, the method further comprises attaching an x-ray energy filter to the first scintillator layer.

In a variation on this embodiment, the method further comprises attaching a third scintillator to a third TFT backplane in the set of TFT backplanes on thin PI layers. The method further comprises bonding at least the third TFT backplane on its PI layer to the second detector.

BRIEF DESCRIPTION OF THE FIGURES

In the figures, like reference numerals refer to the same figure elements.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the disclosed system is not limited to the embodiments shown, but is to be accorded the widest scope consistent with the principles and features disclosed herein.

Overview

Embodiments of the disclosed system solve the problem of energy resolved x-ray imaging by providing a monolithic stack of thin x-ray detector layers. Each layer in the stack can detect a portion of the energy spectrum of transmitted x-rays depending on the absorption of the overlying detectors and of the target object. The system may use energy filters to further differentiate the x-ray energy spectra incident on the different detectors. Thus, the stack can provide energy-resolved information from the combination of images from multiple layers. Other types of ionizing radiation, such as gamma rays, beta particles and neutrons may be detected by the disclosed system.

The disclosed monolithic stack comprises layers containing x-ray detectors, fabricated thinner and closer together than conventional detectors. In an embodiment, the monolithic stack can include multiple x-ray detector layers, wherein a respective detector layer is less than 2 millimeters thick. The x-ray detector layers may include a thin film transistor (TFT) backplane, such as amorphous Si (a-Si) fabricated on a thin polyimide (PI) substrate. Thus, the disclosed structure is compact and reduces the amount of unwanted materials between the detectors.

The system's compact dimensions can help minimize parallax effects. In stacks of multiple conventional x-ray detectors, these parallax effects are large and complicate the alignment of images from different detectors, as will be described below. By reducing parallax effects, the disclosed system improves both accuracy and precision of the resultant combined, energy-resolved images. Accordingly, the system's capacity to combine images accurately enables it to resolve x-ray energy information better than existing systems.

Parallax Effects

Typically, an x-ray detector stack records images taken by multiple detectors. The stack therefore produces multiple images of a single sample. In order to combine these images into consistent energy-resolved information, it is desirable that the geometry of each image should be as similar as possible. But because conventional x-ray detectors are bulky and separated by a large spacing, a parallax effect complicates the alignment of images.

Figure 1:
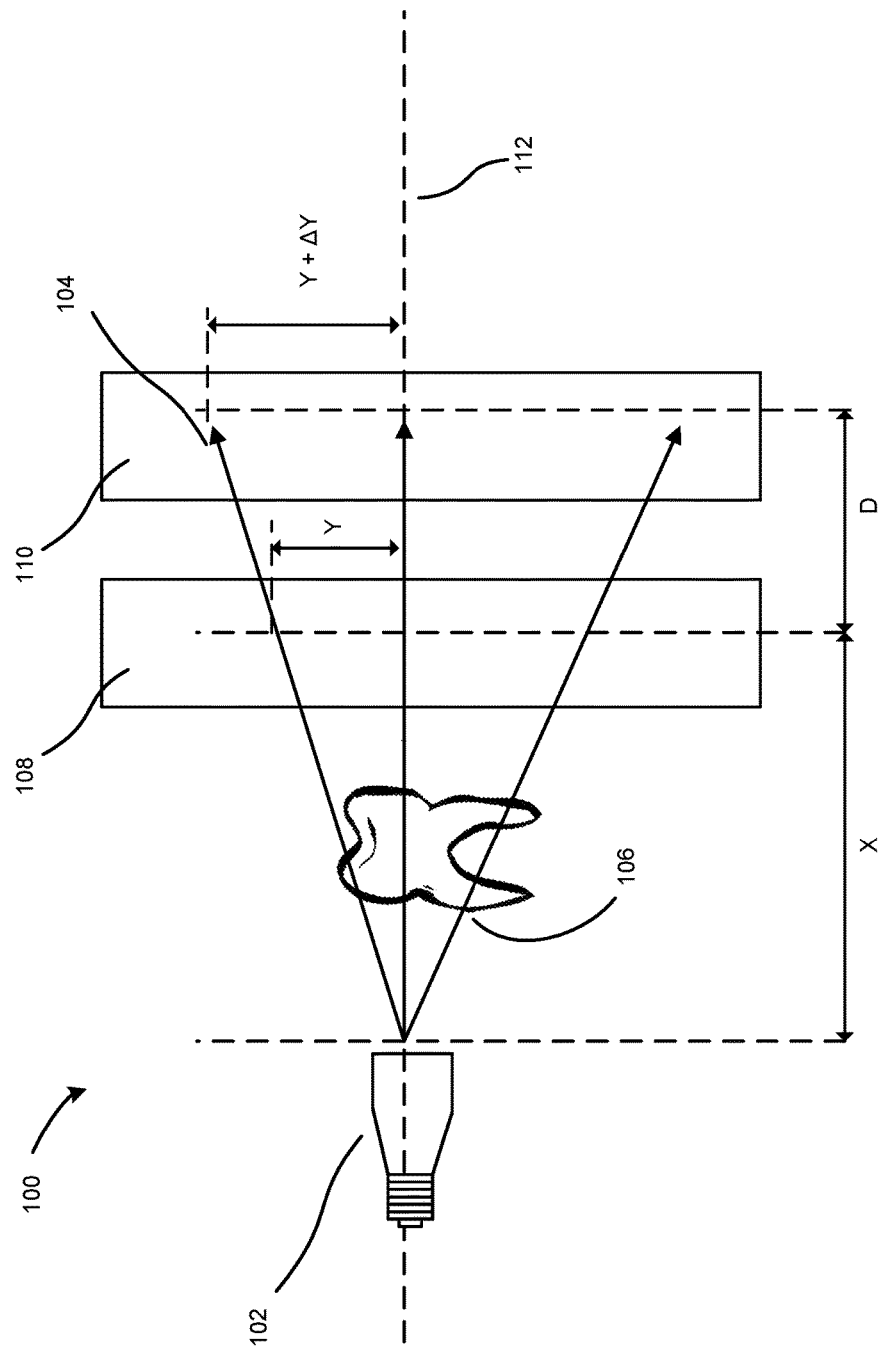
FIG. 1 illustrates parallax shifts in a system of multiple x-ray detectors.

FIG. 1 illustrates parallax shifts in a system 100 of multiple x-ray detectors. In this example, x-ray generator 102 produces x-rays in order to image target 106. X-rays, including off-axis x-ray beam 104, can transmit through target 106 and are absorbed by detectors 108 and 110. Because off-axis x-ray beam 104 travels at an angle relative to the central axis 112 of system 100, beam 104 can arrive at different lateral locations in each detector. As a result of this parallax effect, beam 104 can be detected at different lateral locations by different detectors 108 and 110, and therefore be represented as different pixels within the respective images produced by these detectors.

Specifically, off-axis beam 104 can arrive at detector 108 at a radial distance Y from central axis 112. Because it propagates at an angle to central axis 112, beam 104 arrives at detector 110 at a different distance Y+$\Delta$Y from central axis 112. The difference $\Delta$Y is given by a parallax formula, $\Delta Y = YD/X$, where X is the distance from source 102 to the first detector 108, and D is the distance between detectors.

When this spacing D is large, parallax shift $\Delta$Y can also be large. A large $\Delta$Y can limit the accuracy with which the image features are combined, especially when the value of $\Delta$Y is itself uncertain. For example, the shift $\Delta$Y can be sensitive to the positions of the x-ray source and target, through its dependence on their relative distance X. Yet X often is not recorded when taking an x-ray image, and can result in substantial uncertainty, particularly if target 106 has a large spatial extent or complex shape. Correcting for a large, uncertain parallax shift $\Delta$Y can introduce errors and uncertainty into the relative alignment of the images, making the combined image difficult to compute. A detector stack with minimized spacing D as disclosed herein can reduce the parallax shift ΔY, and, therefore, can resolve transmitted x-ray energy with greater accuracy and precision than existing multi-detector systems.

Operation and Structure of Monolithic X-Ray Detector Stack

The disclosed monolithic detector stack can solve the parallax problem described above. The stack comprises multiple thin x-ray detector layers, with each layer less than 2 millimeters thick. The stack is fabricated as a single unit, as will be described below, with minimal spacing between the layers. The system can obtain energy-resolved information about a target sample by taking x-ray images from multiple detectors in this compact, monolithic stack.

Each detector in the stack can be exposed to a different x-ray energy spectrum, since a respective detector can preferentially absorb part of the radiation (typically in the low-energy portion of the spectrum) before the beam passes on to the next detector. In some embodiments, energy filters can be added to the stack layers to further resolve the x-ray energy spectra incident on the different detectors. Because the disclosed detectors are thinner, and far more closely spaced, than in existing systems, the disclosed monolithic stack system obtains a series of geometrically similar images in different energy bands. Accordingly, the disclosed system can readily combine these images, eliminating the need for substantial corrections for parallax shifts.

Note that to extract energy-resolved images, it is desirable to have knowledge of the x-ray absorption spectrum of the respective detectors. Such a spectrum can be calculated based on known materials, and the results can be confirmed by actual measurements of the x-ray transmission as appropriate. The system can obtain information about the energy resolution by modeling the absorption of a target object and fitting the modeled data to the measured images. The system can further display the absorption of a target object in different energy bands (e.g., by color-coding the image), providing a visual guide to identify the nature of the objects being imaged.

Figure 2A:
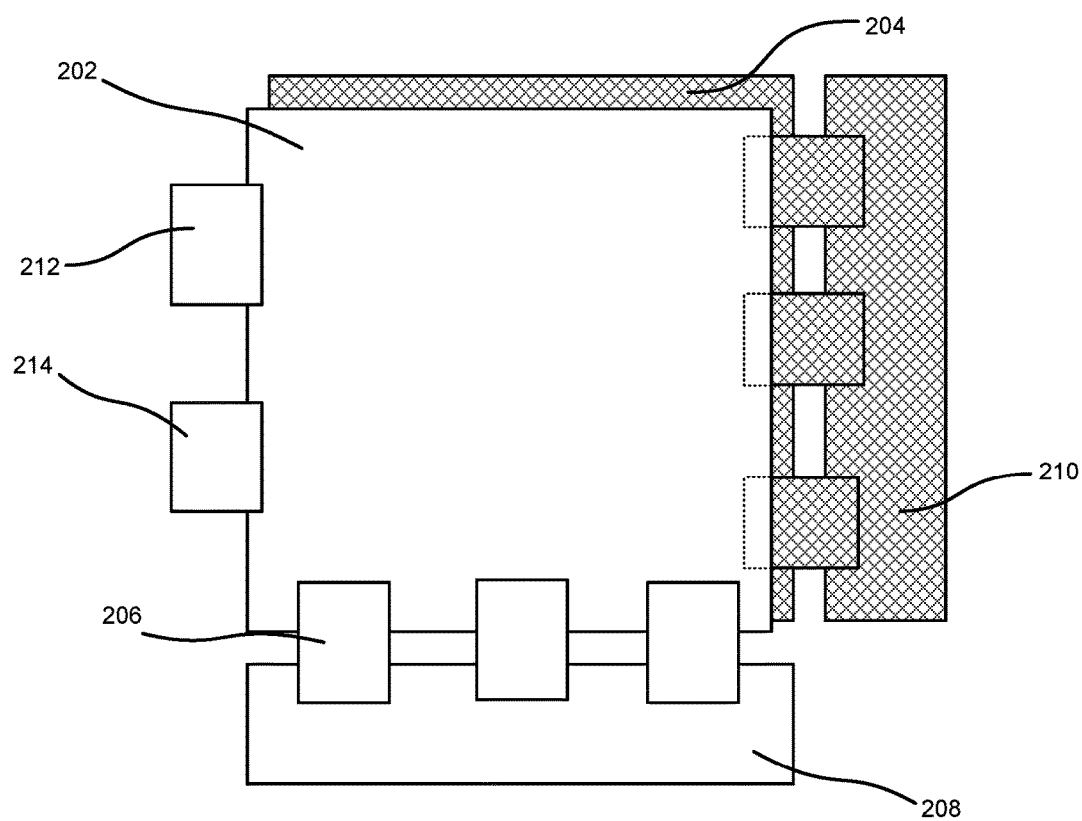
FIG. 2A illustrates a top view of an exemplary monolithic stack of x-ray detector layers, according to one embodiment.

FIG. 2A illustrates a top view of an exemplary monolithic stack of x-ray detector layers, according to one embodiment. A respective layer in the stack, e.g. layers 202 and 204, contains thin x-ray detectors (e.g., based on a-Si TFT arrays), and any other components, such as scintillators, substrates, filters, etc. The respective detector layer can include drive and readout leads, which can be organized for easy connection to control electronics. In this embodiment, layer 202 is attached to data connectors 206 in order to connect to readout printed circuit boards (PCBs) 208 and layer 204 is attached to readout PCB 210. Layer 202 may also be bonded to gate drivers 212 and 214 and layer 204 may be bonded to similar gate drivers (not shown).

As shown, layers 202 and 204 can be oriented perpendicularly to each other in order to provide sufficient space for electronics such as the PCBs, as well as for connections to them. To align the pixels of adjacent layers despite this 90° relative orientation, the detectors can have square-shaped pixels, with the pixel arrays containing approximately equal numbers of rows and columns. Moreover, the system can perform computational corrections for any misalignment between pixels in adjacent layers. In some embodiments, the system can include hardware to perform such corrections and/or to combine energy-resolved images from multiple detector layers. Optionally, the system can do so using firmware or software.

Figure 2B:
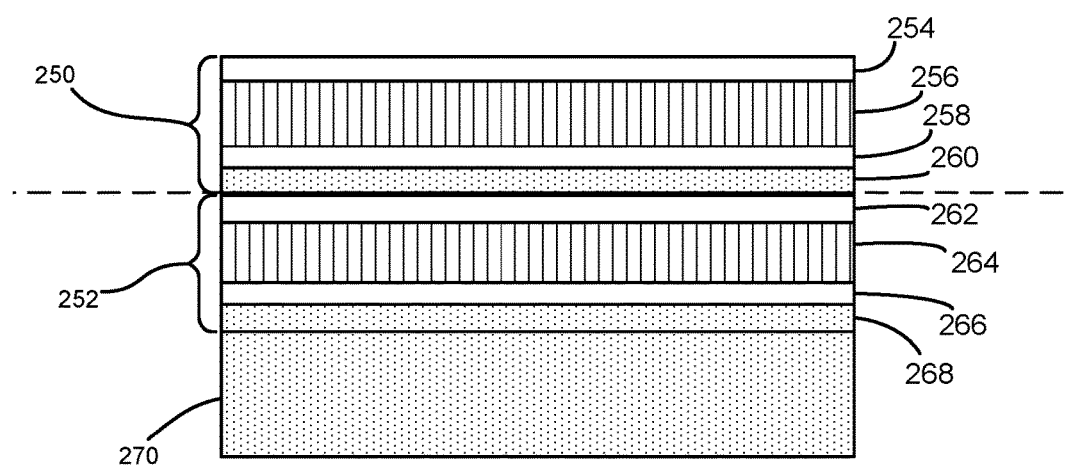
FIG. 2B illustrates a side view of an exemplary monolithic stack of x-ray detector layers, according to one embodiment.

FIG. 2B illustrates a side view of an exemplary monolithic stack of x-ray detector layers 250 and 252, according to one embodiment. First detector layer 250 can include x-ray energy filter 254, scintillator 256, TFT backplane 258, and thin substrate 260. For example, scintillator 256 can be fabricated from materials such as gadolinium oxysulphide (GOS) or cesium iodide (CsI). Note that while CsI has a higher efficiency at converting x-rays to visible light, both materials produce a visible light spectrum that can be efficiently absorbed by photodiodes, such as those in backplane 258. TFT backplane 258 can be fabricated on a thin polyimide (PI) substrate 260, which has a thickness of approximately 10-20 μm. The PI substrate is formed on a rigid carrier, such as glass, in order to support the TFT backplane during fabrication. This carrier is removed before forming the stack. Likewise, second detector layer 252 comprises x-ray energy filter 262, scintillator 264, TFT backplane 266, and thin substrate 268. Finally, in some embodiments, rigid carrier substrate 270 (which may contain, e.g., glass) provides support to the monolithic structure as a whole.

The stack can be readily extended to contain additional detectors, for example a total of four layers. The scintillators may be 200-600 μm thick, and are typically the thickest component of the layers, so that an entire four-layer detector stack can be 1-2 mm thick or less. It is also possible to stack more than four detectors. The thin PI substrate ensures that there is a minimal separation of 10-50 μm between the TFT backplane of one layer and the scintillator of the next layer.

The stack of detectors may be bonded together by suitable adhesive to form a monolithic structure. The bonded monolithic structure ensures that the relative position of pixels in the different detectors is fixed. The detector stack can be contained in a single housing.

Note that the TFT backplanes can be fabricated on flexible substrates 260 and 268, and the most common scintillator materials (GOS and CsI) can also be built on flexible plastic. Thus in some embodiments, the detector stack is flexible, provided that the bottom substrate 270 and integrated filters 254 and 262 are also flexible. However, the stack's flexibility may decrease as the number of detector layers increases.

For the purpose of determining the energy resolution, the light emitted from the scintillator in one layer should not be detected by the TFT backplane in a different layer. This may be accomplished by having an opaque bottom contact to the photodiode and/or a reflective top contact on the scintillator and/or an energy filter that is opaque to photons emitted by the scintillator.

Detector Layer Structure and Variations

Figure 3A:
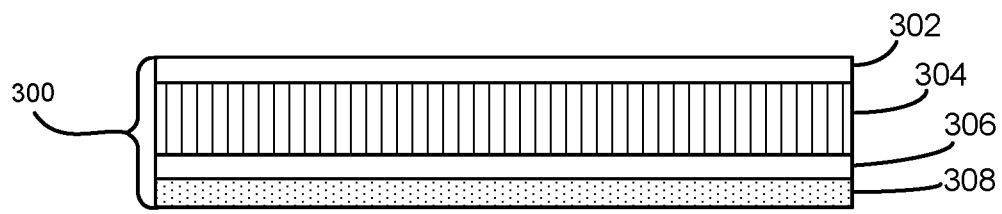
FIG. 3A illustrates an exemplary x-ray detector layer, according to one embodiment.

FIG. 3A illustrates an exemplary x-ray detector layer 300, according to one embodiment. The system can use x-ray energy filter 302 to modify the x-ray energy spectrum transmitted between adjacent layers, so that by design the individual detector layers receive different x-ray energy spectra. Filter 302 may be designed to provide energy-specific x-ray absorption (beyond that of the target and the detectors themselves) in order to adjust the energy of the incident x-ray flux. Filter 302 may be produced from a variety of materials, e.g. metals of different atomic mass and/or thickness, to engineer the filter's x-ray absorption. The choice of absorbers can be based on the desired energy resolution properties for a particular application.

As described above, detector layer 300 (for indirect x-ray detection) can also contain scintillator 304 made from GOS or CsI, which can efficiently absorb x-rays and produce visible-spectrum photons. Backplane 306, which may be fabricated from amorphous Si (a-Si), can include an array of photodiodes and TFTs to absorb these visible photons, and record them as pixels of a digital image. In some embodiments, the TFT backplane can be made by a variety of processes, including using poly-silicon or oxide semiconductors for the transistors.

Figure 3B:
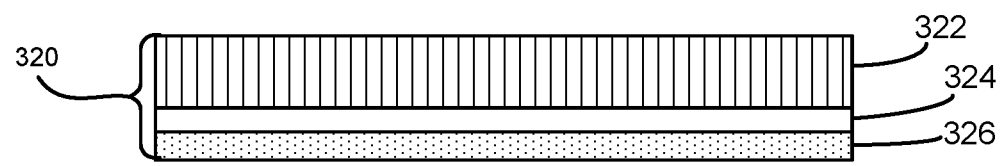
FIG. 3B illustrates an exemplary x-ray detector layer without an energy filter, according to one embodiment.

Numerous variations are possible to the basic detector layer structure described above. In some embodiments, one or more detector layers in the monolithic stack may lack an energy filter. FIG. 3B illustrates an exemplary x-ray detector layer 320 without an energy filter, according to one embodiment. In this case, the received energy spectrum can still differ among the detectors because each detector layer, specifically the scintillator, can preferentially absorb part of the x-ray spectrum. Depending on the detector's design and materials, typically this would be the low-energy end of the spectrum. Thus, detector layer 320 may contain only scintillator 322, TFT backplane 324, and thin substrate 326.

Figure 3C:
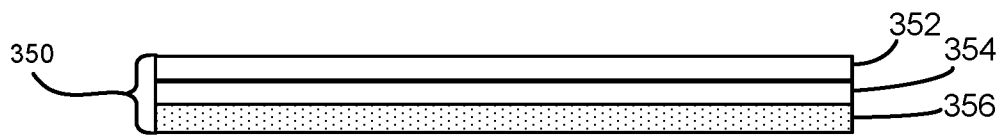
FIG. 3C illustrates an exemplary direct x-ray detector layer, according to one embodiment.

In addition to indirect detectors, the system can make use of one or more layers of direct detector arrays. Such direct detectors convert x-rays directly to electric charge, i.e. without scintillator components that convert x-rays to visible light as an intermediate product. FIG. 3C illustrates an exemplary direct x-ray detector layer 350, according to one embodiment. In this case, the scintillator and the a-Si photodiodes are replaced by an x-ray photoconductor 352 such as selenium, to convert the incident x-rays to an electrical signal. The system can still use a similar TFT backplane 354 to record the image as a pixel array and a substrate 356 to support layer 350.

Note that the x-ray absorption spectrum of selenium differs from the common scintillators, such as GOS and CsI. Therefore, both types of detector layers can be used in the same stack, to meet energy resolution requirements as an alternative to adding filter material. The indirect detector layer can also contain an optional energy filter.

Figure 3D:
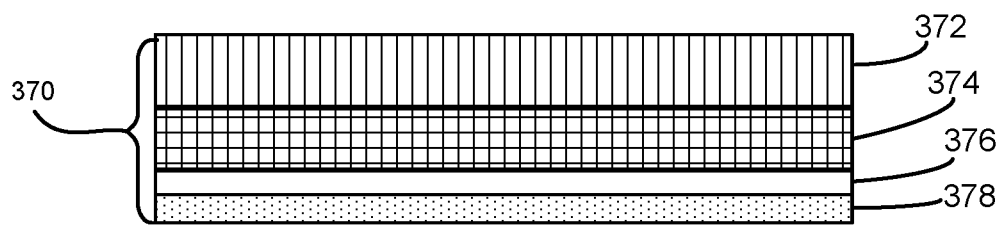
FIG. 3D illustrates an exemplary neutron detector layer, according to one embodiment.

The monolithic detector stack disclosed herein is not limited to x-ray energy resolution, and may be used for additional purposes. For example, a single stack can contain multiple detectors in order to simultaneously sense multiple radiation types, such as x-rays and neutrons. FIG. 3D illustrates an exemplary neutron detector layer 370, according to one embodiment. As shown, layer 370 can contain scintillator 372 and photodetector 374 to convert neutrons to visible light and an electrical signal. Note that, as for x-ray detection, scintillators are a common tool for neutron detection. In some embodiments, other neutron detectors such as gas proportional detectors or activation detectors may be used. Neutron detector layer 370 may include optional backplane 376 such as a-Si to digitize the image of detected neutrons, and substrate 378 for support. In some embodiments, detectors for other forms of ionizing radiation are possible, e.g. gamma rays or beta rays.

Assembling a Monolithic Stack of Detector Layers

This section describes exemplary processes for assembling the disclosed monolithic detector stack system.

Figure 4:
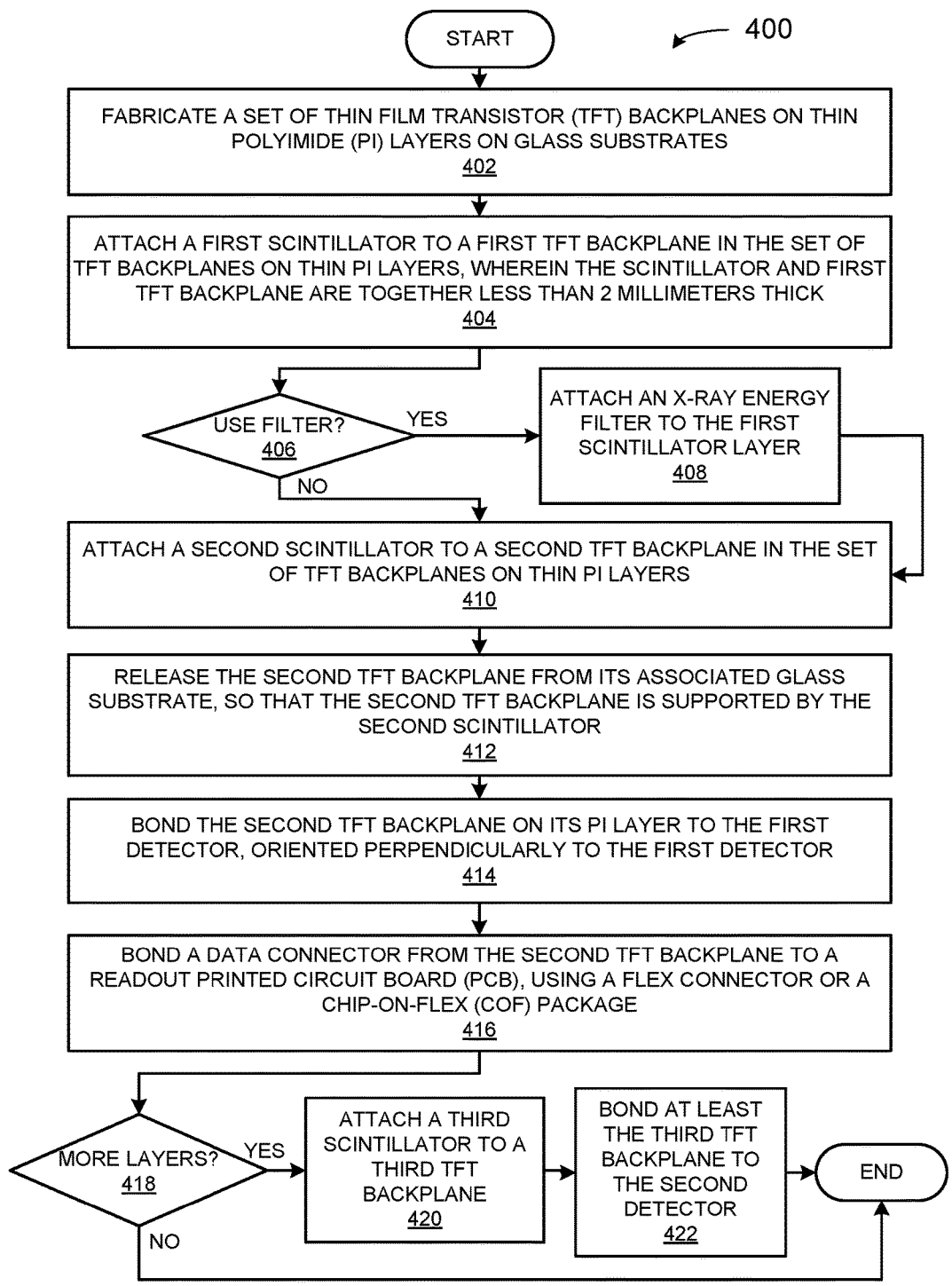
FIG. 4 presents a block diagram illustrating a method for assembling a monolithic stack of x-ray detector layers, according to one embodiment.

FIG. 4 presents a block diagram illustrating a method 400 for assembling a monolithic stack of x-ray detector layers, according to one embodiment. The method involves fabricating a set of thin film transistor (TFT) backplanes on thin polyimide (PI) layers on the carrier glass substrates (operation 402). The thin PI layers can have a thickness of about 10-20 μm. This fabrication can be done using existing facilities.

The assembly method next involves attaching a first scintillator to a first TFT backplane in the set of TFT backplanes on thin PI layers (operation 404). The scintillator, first TFT backplane, and PI layer can be overall less than 2 millimeters thick. In some embodiments, these components are overall less than 1 millimeter thick, e.g. the scintillators may be 200-600 μm thick, and may be the thickest component.

In some embodiments, the method can be used to assemble a monolithic stack with energy filters in the respective layers. In the case of assembling detector layers with energy filters (operation 406), the method can involve attaching an x-ray energy filter to the first scintillator layer (operation 408).

Subsequently, a data connector from the first TFT backplane can be bonded to a readout printed circuit board (PCB), using a flex connector or a chip-on-flex (COF) package. This completes assembling the first detector layer.

The method then involves attaching a second scintillator to a second TFT backplane in the set of TFT backplanes on thin PI layers (operation 410). The second TFT backplane can be released from its associated carrier glass substrate, using techniques known in the art, so that the second TFT backplane is supported by the second scintillator (operation 412). The second TFT backplane can then be bonded on its PI layer to the first detector, oriented perpendicularly to the first detector (operation 414). Subsequently, a data connector from the second TFT backplane can be bonded to a readout printed circuit board (PCB), using a flex connector or a chip-on-flex (COF) package (operation 416). This completes assembling the second detector layer.

In the case of assembling a monolithic stack containing more than two detector layers (operation 418), the method involves attaching a third scintillator to a third TFT backplane in the set of TFT backplanes on thin PI layers (operation 420). The third TFT backplane can be released from its associated glass substrate. The third TFT backplane on its PI layer can then be bonded to the second detector (operation 422), and a data connector from the third TFT backplane can be bonded to a readout PCB, using a flex connector or a COF package. These steps (operations 420 and 422) can be repeated to attach additional detector layers, e.g. to assemble a total of four or more layers.

In some cases (for example with more than two layers), bonding to the additional PCBs on the same side of the TFT array stack may be difficult, but is nevertheless possible. For example, one PCB can be bent out of the way while another is bonded.

As described above, the disclosed system can also include direct detectors, or can include poly-silicon or oxide semiconductor transistors. To assemble a direct detector layer, instead of attaching the scintillator (e.g., operations 404 or 410), the method can include attaching an x-ray photoconductor such as selenium. Note that the direct detector can still be based on a similar TFT backplane as in the indirect detector. As another option, the method can include utilizing poly-silicon or oxide semiconductor transistors instead of a-Si to fabricate the TFT backplane. Moreover, the method can include attaching a detector for neutrons or other radiation types instead of the indirect x-ray detector. Different types of layers can also be mixed within a single stack, so the assembly options disclosed here may apply to any or all of the layers in the stack.

Figure 5A:
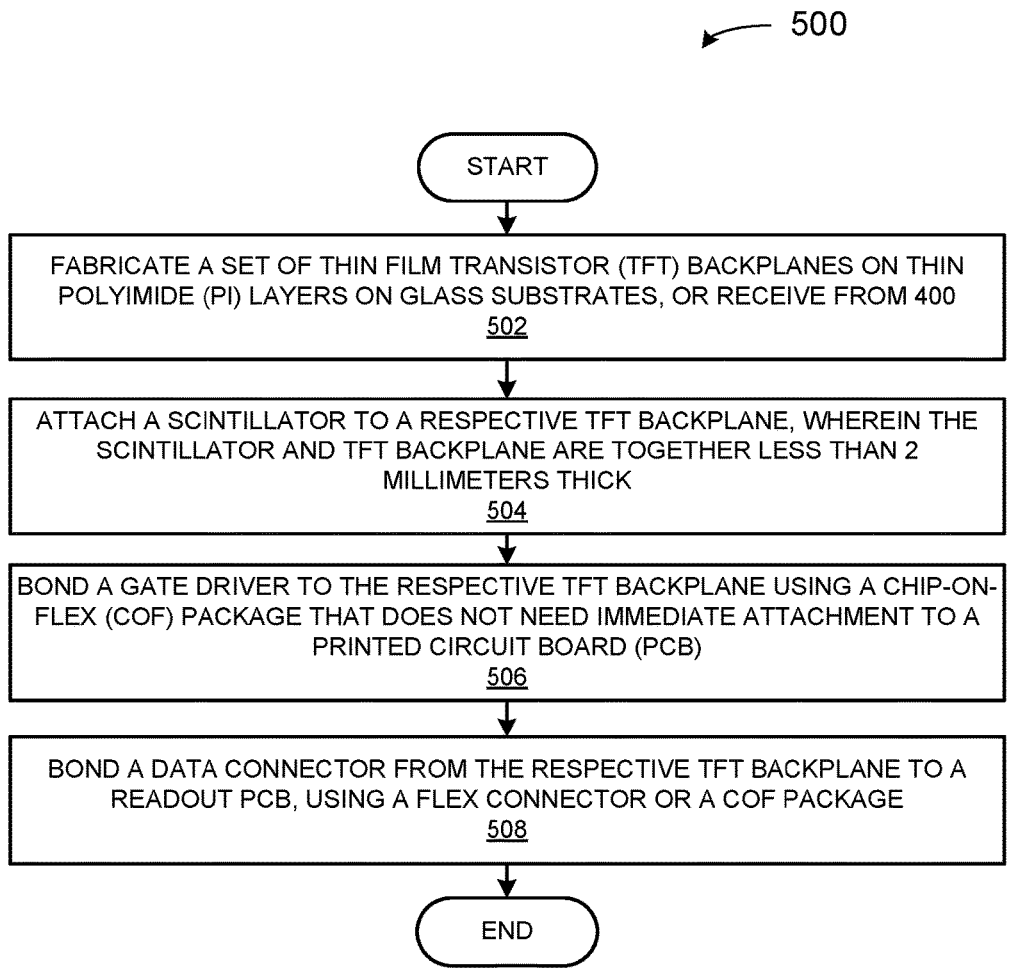
FIG. 5A presents a block diagram illustrating a method for forming electronic connections to a monolithic stack of x-ray detector layers, according to one embodiment.

The assembly process can include further variations to method 400 described above, such as additional electronic connections or bonding to an alternative substrate. FIG. 5A presents a block diagram illustrating a method 500 for forming electronic connections to a monolithic stack of x-ray detector layers, according to one embodiment. During operation, one can fabricate a set of TFT backplanes on thin PI layers on glass substrates (operation 502), as described in relation to method 400. A scintillator can be attached to a respective TFT backplane in the set of TFT backplanes on thin PI layers, wherein the scintillator and first TFT backplane are jointly less than 2 millimeters thick (operation 504). In some embodiments, the scintillator and first TFT backplane together can be less than 1 millimeter thick. The method can further include bonding a gate driver to the respective TFT backplane using a COF package that does not need immediate attachment to a PCB (operation 506). A data connector from the respective TFT backplane can then be bonded to a readout PCB, using a flex connector or a COF package (operation 508).

Figure 5B:
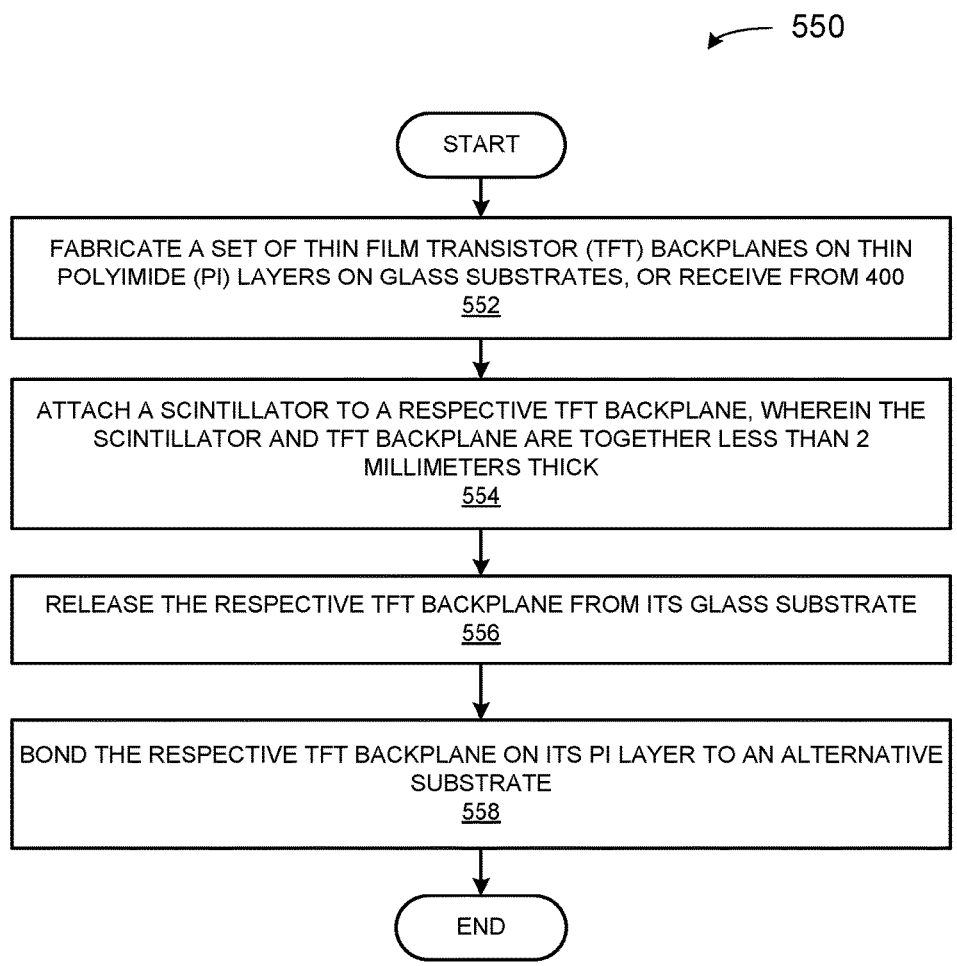
FIG. 5B presents a block diagram illustrating a method for bonding a thin film transistor (TFT) to an alternative substrate within a monolithic stack of x-ray detector layers, according to one embodiment.

FIG. 5B presents a block diagram illustrating a method 550 for bonding a thin film transistor (TFT) to an alternative substrate within a monolithic stack of x-ray detector layers, according to one embodiment. One can fabricate a set of TFT backplanes on thin PI layers on glass substrates (operation 552), as described in relation to method 400. A scintillator can then be attached to a respective TFT backplane in the set of TFT backplanes on thin PI layers, wherein the scintillator and first TFT backplane together are less than 2 millimeters thick (operation 554). In some embodiments, these components are less than 1 millimeter thick. The method further involves releasing the respective TFT backplane from its glass substrate (operation 556). The respective TFT backplane on its PI layer can then be bonded to an alternative substrate (operation 558).

System Architecture

Figure 6:
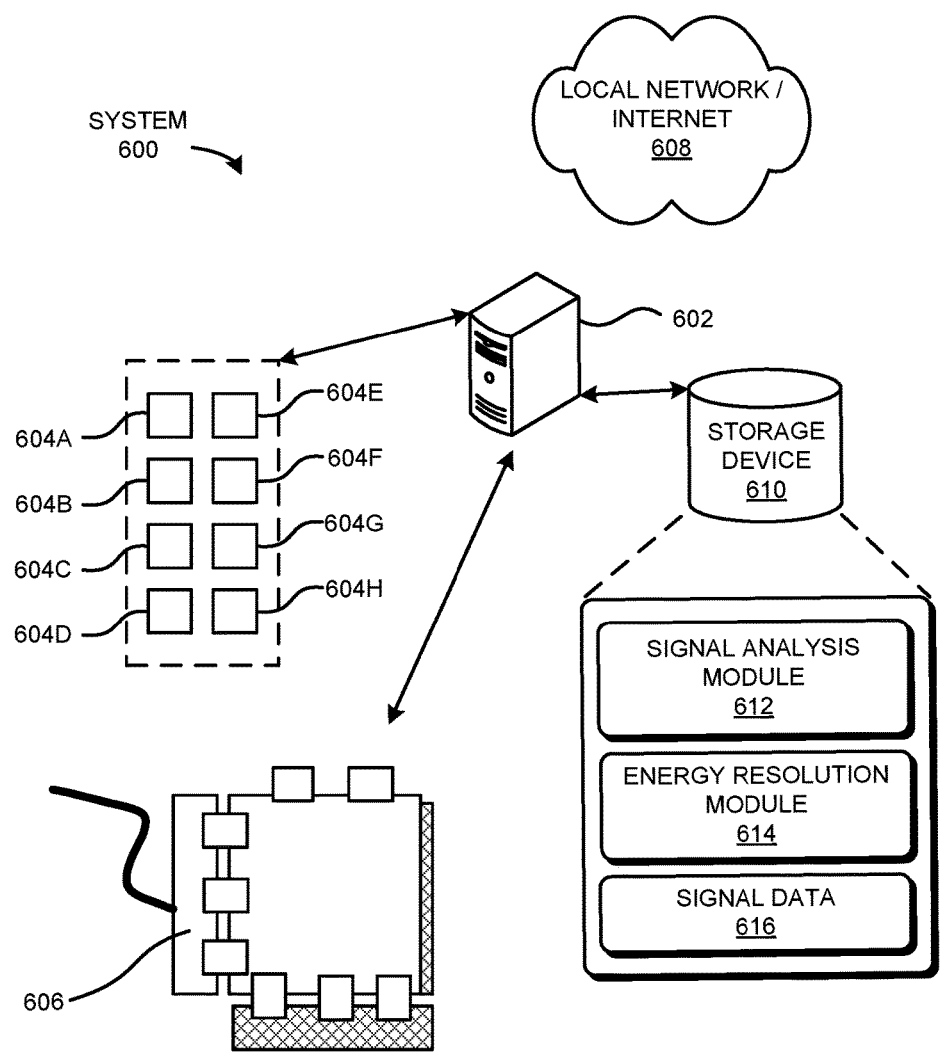
FIG. 6 presents a block diagram illustrating an exemplary architecture of an energy resolved x-ray imaging system, according to embodiments.

FIG. 6 presents a block diagram illustrating an exemplary architecture of an energy resolved x-ray imaging system 600, according to embodiments. Energy resolved x-ray imaging system 600 may analyze detector pixel data and/or align or combine energy-resolved images from multiple detector layers.

Energy resolved x-ray imaging system 600 may include a signal analysis module 612 and energy resolution module 614 installed on a storage device 610 coupled to a computing device 602. Note that in various implementations of the disclosed system, computing device 602 may include a server, computer, and/or mobile device. Computing device 602 may be coupled via one or more network interfaces to one or more networks, such as local network, wireless network, or Internet 608. System 600 may receive data 616 describing detector signals, and store such data in storage device 610. System 600 may read the code for signal analysis module 612 and energy resolution module 614, and signal data 616 from storage device 610. System 600 may dynamically divide such signal data and assign them to processors, such as processors 610A-610H, which operate on the assigned signal data.

The detector pixel data analysis and/or energy-resolution operations described herein can also be integrated into hardware modules or apparatus. These modules or apparatus may include, but are not limited to, a printed circuit board (PCB), a chip-on-flex (COF), an analog to digital converter (ADC), an application-specific integrated circuit (ASIC) chip, a field-programmable gate array (FPGA), a system on a chip (SoC), and/or other circuit devices now known or later developed. When the hardware modules or apparatus are activated, they perform the circuit functions included within them.

The foregoing descriptions of various embodiments have been presented only for purposes of illustration and description. They are not intended to be exhaustive or to limit the present systems and methods to the forms disclosed. Accordingly, many modifications and variations will be apparent to practitioners skilled in the art. Additionally, the above disclosure is not intended to limit the present systems and methods.

What is claimed is:

1. An energy-spectrum-resolved digital detector of ionizing radiation, the detector comprising:
    a monolithic stack of multiple adjacent radiation detector layers:
        wherein each radiation detector layer of the multiple adjacent radiation detector layers comprises a four-layer structure comprising a radiation energy filter, a radiation converter, a thin film transistor (TFT) backplane, and a polyimide substrate, wherein the TFT backplane is positioned on and in direct contact with the polyimide substrate;
        wherein two adjacent radiation detector layers are in direct contact with each other, with the polyimide substrate of a first radiation detector layer being in direct physical contact with the radiation energy filter of an immediately adjacent second radiation detector layer, thereby reducing a parallax effect;
        wherein a thickness of the four-layer structure that comprises the radiation energy filter, the radiation converter, the TFT backplane, and the polyimide substrate is less than one millimeter; and
        wherein different radiation energy filters of the multiple adjacent radiation detector layers are each configured to modify a different portion of an energy spectrum of the ionizing radiation in such a way that each radiation detector layer detects a different portion of the energy spectrum of the ionizing radiation, thereby facilitating energy-spectrum-resolved detection of the ionizing radiation.

2. The energy-spectrum-resolved digital detector of claim 1, wherein TFT backplanes in two adjacent radiation detector layers are oriented at a substantially right angle about an axis along a height of the stack to facilitate connection to electronics.

3. The energy-spectrum-resolved digital detector of claim 1, wherein the radiation converter comprises a scintillator, and wherein the TFT backplane comprises a TFT addressable photodiode array.

4. The energy-spectrum-resolved digital detector of claim 3, wherein the scintillator comprises gadolinium oxysulphide (GOS) or cesium iodide (CsI), and wherein the TFT addressable photodiode array comprises amorphous silicon (a-Si).

5. The energy-spectrum-resolved digital detector of claim 1, wherein the radiation converter comprises an x-ray photoconductor.

6. The energy-spectrum-resolved digital detector of claim 5, wherein the x-ray photoconductor comprises selenium.

7. The energy-spectrum-resolved digital detector of claim 1, wherein the radiation converter is configured to function as a neutron detector.

8. A system for providing energy-spectrum-resolved detection of ionizing radiation, the system comprising:
    a monolithic stack of multiple adjacent radiation detector layers:
        wherein each radiation detector layer of the multiple adjacent radiation detector layers comprises a four-layer structure comprising a radiation energy filter, a radiation converter, a thin-film transistor (TFT) backplane, and a polyimide substrate, wherein the TFT backplane is positioned on and in direct contact with the polyimide substrate;

wherein two adjacent radiation detector layers are in direct contact with each other, with the polyimide substrate of a first radiation detector layer being in direct physical contact with the radiation energy filter of an immediately adjacent second radiation detector layer, thereby reducing a parallax effect;

wherein a thickness of the four-layer structure that comprises the radiation energy filter, the radiation converter, the TFT backplane, and the polyimide substrate is less than one millimeter; and wherein different radiation energy filters of the multiple adjacent radiation detector layers are each configured to modify a different portion of an energy spectrum of the ionizing radiation in such a way that each radiation detector layer detects a different portion of the energy spectrum of the ionizing radiation, thereby facilitating energy-spectrum-resolved detection of the ionizing radiation;

one or more printed circuit boards (PCBs);

one or more data connectors connecting the stack of radiation detector layers and the one or more PCBs; and one or more gate drivers attached to the monolithic stack of radiation detector layers.

9. The system of claim 8, wherein respective TFT backplanes in two adjacent radiation detector layers are positioned at a substantially right angle about an axis along a height of the stack to facilitate connection to electronics.

10. The system of claim 8, wherein the radiation converter comprises a scintillator, and wherein the TFT backplane comprises a TFT addressable photodiode array.

11. The system of claim 10, wherein the scintillator comprises gadolinium oxysulphide (GOS) or cesium iodide (CsI), and wherein the TFT addressable photodiode array comprises amorphous silicon (a-Si).

12. The system of claim 8, wherein the radiation converter comprises an x-ray photoconductor, and wherein the TFT backplane comprises a TFT addressable photodiode array.

13. The system of claim 8, wherein the radiation converter is configured to function as a neutron detector.

14. A method for assembling a stack of digital ionizing radiation detector layers, the method comprising:

fabricating a first thin film transistor (TFT) addressable photodiode backplane on a first thin polyimide substrate mounted on a carrier;

attaching a first radiation converter and a first radiation energy filter to the first TFT backplane to form a first ionizing radiation detector, which comprises a first four-layer structure comprising the first radiation energy filter, the first radiation converter, the first TFT backplane, and the first thin polyimide substrate;

releasing the first ionizing radiation detector from the carrier, thereby allowing the first TFT backplane to be supported by the first radiation converter and the first thin polyimide substrate;

bonding the first ionizing radiation detector to a second ionizing radiation detector, which comprises a second four-layer structure comprising a second radiation energy filter, a second radiation converter, a second TFT backplane, and a second thin polyimide substrate, wherein a thickness of the first or second four-layer structure is less than one millimeter;

wherein the first and second ionizing radiation detectors are in direct contact with each other, with the second polyimide substrate being in direct physical contact with the first radiation energy filter, thereby reducing a parallax effect;

wherein the first and second radiation energy filters are configured to each modify a different portion of an energy spectrum of the ionizing radiation in such a way that each ionizing radiation detector detects a different portion of the energy spectrum of ionizing radiation, thereby facilitating energy-spectrum-resolved detection of ionizing radiation; and bonding a data connector from the first TFT backplane to a readout printed circuit board (PCB).

15. The method of claim 14, wherein attaching the first radiation converter to the first TFT backplane further comprises bonding a gate driver to the first TFT backplane using a chip-on-flex (COF) package.

16. The method of claim 14, further comprising:

releasing the first TFT backplane from a corresponding glass substrate; and bonding the first TFT backplane to an alternative substrate.

17. The method of claim 14, further comprising:

forming a third ionizing radiation detector, which comprises a third radiation converter, a third radiation energy filter, a third TFT backplane, and a third thin polyimide substrate; and bonding at least the third ionizing radiation detector to the second ionizing radiation detector.

\* \* \* \* \*